(12) United States Patent
Jacobsen

(10) Patent No.: US 10,420,779 B2
(45) Date of Patent: Sep. 24, 2019

(54) FUSIDIC ACID CREAM AND METHOD FOR THE PREPARATION THEREOF

(71) Applicant: Hyloris Pharmaceuticals SA, Liège (BE)

(72) Inventor: Thomas Jacobsen, Leuven (BE)

(73) Assignee: Hyloris Pharmaceuticals SA, Liège (BE)

( * ) Notice: Subject to any disclaimer, the term of this patent is extended or adjusted under 35 U.S.C. 154(b) by 0 days.

(21) Appl. No.: 15/133,606

(22) Filed: Apr. 20, 2016

(65) Prior Publication Data

US 2016/0303142 A1    Oct. 20, 2016

(30) Foreign Application Priority Data

Apr. 20, 2015 (BE) .................................. 2015/5256

(51) Int. Cl.
| | | |
|---|---|---|
| *A61K 31/575* | (2006.01) | |
| *A61K 9/00* | (2006.01) | |
| *A61K 47/10* | (2017.01) | |
| *A61K 9/06* | (2006.01) | |

(52) U.S. Cl.
CPC .......... *A61K 31/575* (2013.01); *A61K 9/0014* (2013.01); *A61K 9/06* (2013.01); *A61K 47/10* (2013.01)

(58) Field of Classification Search
None
See application file for complete search history.

(56) References Cited

U.S. PATENT DOCUMENTS

| | | | | | |
|---|---|---|---|---|---|
| 5,654,293 | A | * | 8/1997 | François | ................ A61K 31/57 514/171 |
| 2011/0009375 | A1 | * | 1/2011 | Jones | ................... A61K 31/575 514/182 |

FOREIGN PATENT DOCUMENTS

WO    WO 2010/070589 A2    6/2010

OTHER PUBLICATIONS

Anonymous: "Package Leaflet: Information for the User, Fucidin® 20mg/g Cream; Other medicines and Fucidin cream; Pregnancy and breast-feeding," downloaded from the Internet: URL:https://www.hpra.ie/img/uploaded/swedocuments/2140144.PPA1151_086_01.46d979f6-5aad-4996-a2ad-db9b11adf97b.000001Fucidin%20cream%20PIL.140130.pdf, (Oct. 29, 2013), 2 pages.
Mahalingam et al., "Semisolid Dosages: Ointments, Creams, and Gels," *Pharmaceutical Sciences Encyclopedia: Drug Discovery, Development, and Manufacturing*, edited by Shayne C. Gad, John Wiley & Sons, Inc., pp. 1-46 (2010).
Musmade et al., "Fusidic Acid—Topical Antimicrobial in the Management of *Staphylococcus aureus*," *International Journal of Pharmacy and Pharmaceutical Sciences*, vol. 5, Suppl. 4, pp. 381-390 (2013).

* cited by examiner

*Primary Examiner* — David J Blanchard
*Assistant Examiner* — Sarah J Chickos
(74) *Attorney, Agent, or Firm* — Knobbe, Martens, Olson & Bear, LLP

(57) ABSTRACT

The present invention relates to a composition appropriate for topical application, containing fusidic acid. The homogeneity of the fusidic acid is 90% to 110% of the suggested fusidic acid content, and the amount of air present in the cream is lower than 5 vol %. Furthermore, the present invention also relates to a method for preparing the composition. First, a placebo cream and a suspension of fusidic acid are prepared, which are subsequently mixed at a temperature above the melting point of the placebo cream.

7 Claims, No Drawings

FUSIDIC ACID CREAM AND METHOD FOR THE PREPARATION THEREOF

TECHNICAL DOMAIN

The present invention relates to a fusidic acid cream and a method for the preparation of such a cream. In particular, the invention relates to a method for obtaining a homogenous fusidic acid cream comprising a small amount of air.

STATE OF THE ART

Fusidic acid is a bacteriostatic antibiotic, which prevents bacteria to multiply. Fusidic acid shows this effect with certain strains of *Neisseria* and gram positive bacteria such as *Staphylococcus aureus, Streptococcus* and *Corynebacterium minutissimum*. Fusidic acid is represented by the chemical structure in formula (I):

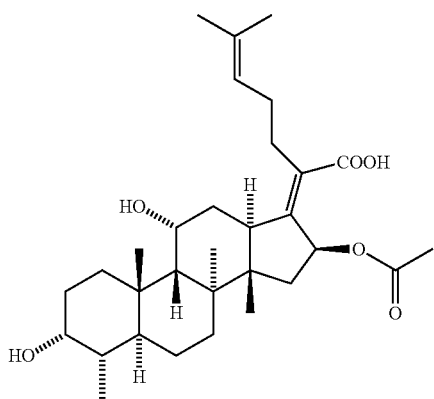

(I)

Fusidic acid is mostly applied topically and therefore, the known formulations are in the form of an ointment, a cream, a gel or eye drops.

A problem of fusidic acid is that it is not easily soluble in the common solvents for topical applications. For example, fusidic acid does not solve in water, or non-polar organic solvents. Fusidic acid does solve in polar organic solvents, such as alcohols and DMSO. The latter solvents can however not be used in topical applications as they have side effects when applied to the skin. Therefore, for obtaining a fusidic acid cream, no standard techniques can be used that can be used for formulating creams. The preparation of fusidic acid cream often requires long mixing times, and these long mixing times result in more air that is mixed under the cream. As a result, the cream doesn't feel smooth, but granular. Hence, the comfort for the user decreases. The application of the cream feels rough. The user has the feeling that the cream has not been mixed properly or that the shelf time of the cream has expired. An additional disadvantage of the presence of larger amounts of air in a cream is that air comprises oxygen gas. This oxygen gas can oxidize the ingredients of the cream. Side products can be developed and the shelf time of the cream can decrease. The sensitivity to oxidation of fusidic acid is illustrated in EP 2 419 087, this document describes that the oxidation problem is all the bigger as the particle size of the fusidic acid is smaller.

The present invention aims to find a solution for at least some of the above-mentioned problems. The invention aims to prepare a homogenous fusidic acid cream comprising only a small amount of air.

SUMMARY OF THE INVENTION

In a first aspect, the invention provides a method for preparing a topical fusidic acid composition, comprising the following steps:
a) making a suspension of fusidic acid in an aqueous phase;
b) melting and mixing the ingredients to obtain a placebo cream;
c) heating the placebo cream above its melting point;
d) mixing the suspension of step a) with the placebo cream of step c);
wherein the mixing in step d) is realized at a temperature of minimum 5° C. above the melting point of said placebo cream.

By mixing at a temperature above the melting point of the placebo cream, the solid fusidic acid particles can mix more easily with the placebo cream and thus a homogenous distribution is obtained of the active substance in the final fusidic acid cream. By more easily mixing the placebo cream and the fusidic acid suspension, one has to mix less and at a lower speed. Hence, the amount of air that is mixed in the cream, is decreased and the cream gets a smoother texture and the oxidation of the active substance as well as of other adjuvants is decreased because less oxygen gas is introduced during the mixing.

In a second aspect, the invention provides a fusidic acid composition used for topical application, comprising:
 0.5 to 5.0 percent by weight of fusidic acid,
 5.0 to 20.0 percent by weight of hexadecanol,
 1.0 to 15.0 percent by weight of white soft paraffin;
 5.0 to 20.0 percent by weight of liquid paraffin;
 0.001 to 0.010 percent by weight of butyl hydroxyanisol,
 0.1 to 0.5 percent by weight of sorbic acid or an equivalent as salt thereof;
 5.0 to 20.0 percent by weight of glycerol,
 1.0 to 15.0 percent by weight of polysorbate; and
 water;
wherein the homogeneity of the fusidic acid content in the composition is 90% to 110%; and the amount of air present in the cream is lower than 5 vol %.

The composition with a high homogeneity and a low amount of air has the advantage that the composition feels smooth and still doesn't lose its homogeneity. A lower homogeneity make a correct treatment more difficult if not impossible because the patient doesn't know how much active substance he/she applies. As a result of a low homogeneity, the effectively applied amount of fusidic acid varies, as a result of which a patient sometimes applies too much and sometimes too little for an effective treatment of his/her complaint. When applying too little fusidic acid, the bacteria do not stop multiplying. Hence, the treatment lasts longer, and the bacteria that are exposed to fusidic acid, can develop resistance. When applying too much fusidic acid, the side effects of fusidic acid such as irritation, itching and redness increase.

In a third aspect, the invention provides a tube made of aluminium comprising a fusidic acid composition according to an embodiment of a composition according to the invention, wherein the aluminium inside of the tube is provided with an epoxy coating.

The use of an epoxy coating ensures that both the fusidic acid and the adjuvants cannot react with the aluminium of the tube. In this way, they cannot be converted into impurities possibly having a negative effect on side effects and shelf time.

In a fourth aspect, the invention provides a composition according to an embodiment of the invention for use in the treatment of skin infections caused by bacteria that are sensitive to fusidic acid.

DETAILED DESCRIPTION

Unless otherwise specified, all terms used in the description of the invention, including technical and scientific terms, shall have the meaning as they are generally understood by the worker in the technical field of the invention. For a better understanding of the description of the invention, the following terms are explained specifically.

The citation of numeric intervals by means of end points comprises all integers, fractions and/or real numbers between the end points, including these end points.

In a first aspect, the invention provides a method for preparing a topical composition, preferably a fusidic acid cream, comprising the steps of:
  a) making a suspension of fusidic acid in an aqueous phase;
  b) melting and mixing the ingredients to obtain a placebo cream;
  c) heating the placebo cream above its melting point;
  d) mixing the suspension of step a) with the placebo cream of step c);
wherein the mixing in step d) is realized at a temperature of minimum 5° C. above the melting point of said placebo cream.

Fusidic acid does not easily solve in water and hydrophobic solvents. Fusidic acid can however be solved in alcohols and polar organic solvents such as DMSO. However, such polar organic solvents have negative side effects when they are used in a cream. For example, they withdraw lipids from the skin, as a result of which the skin dries out. Therefore, these polar organic solvents are not used in the composition. Hence, the cream is a suspension of solid fusidic acid particles in an oil-in-water emulsion. To obtain a cream wherein the active substance, that is fusidic acid, is homogenously spread into the cream, a suspension of fusidic acid in an aqueous phase is made and a placebo cream of the other ingredients is separately made. Preferably, 0.5 to 5.0, more preferably 1.0 to 4.0, still more preferably 1.5 to 3.0 and most preferably 2.0 percent in weight of fusidic acid is added to obtain the said suspension, this percentage in weight is expressed in relation to the total weight of the final cream. It appears that fusidic acid shows an antibacterial effect in this range. Higher concentrations of fusidic acid lead to side effects such as irritation, itching or redness.

The term "aqueous phase" refers to a liquid phase that can be solved with water. The aqueous phase can comprise polar organic components such as glycerol. The polar organic components can by itself make up the majority of the aqueous phase, for example an 80 vol % glycerol in water solution or an 85 vol % glycerol in water solution.

The term "placebo cream" refers to a cream that does not comprise any active substances, but does comprise a number of adjuvants, and forms a formulation in itself that does not disintegrate in a period of at least one month.

The term "semi-solid substance" primarily is a technical term and refers to a physical term for something on the border between a solid substance and a liquid. As with a solid substance, a semi-solid substance can bear its own weight and keep its shape. However, a semi-solid substance also shows characteristics of a liquid. Such as for example, taking the shape of a recipient and the possibility to flow under the influence of an external pressure. The terms semi-solid, quasi-solid and semi-liquid are synonyms.

This placebo cream is a semi-solid substance, and is heated above its own melting point, preferably at least 5 degrees Celsius above the melting point, more preferably at least 7 degrees Celsius above the melting point, still more preferably at least 10 degrees Celsius above the melting point, even more preferably at least 15 degrees Celsius above the melting point and most preferably to at least 20 degrees Celsius above the melting point. As a result, all ingredients in the placebo cream become liquid. In this fully liquid state, the suspension of fusidic acid is added to the placebo cream. As a result, the solid fusidic acid particles can more easily mix with the placebo cream and thus a homogenous distribution is obtained of the active substance in the final fusidic acid cream. By more easily mixing the placebo cream and the fusidic acid suspension, one has to mix less and at a lower speed. Hence, the amount of air that is mixed in the cream, is decreased and the cream gets a smoother texture and the oxidation of the active substance as well as of other adjuvants is decreased because less oxygen gas is introduced during the mixing.

In a preferred embodiment, the mixing of step d) is realized under decreased air pressure, preferably at an air pressure below 101.325 kPa, more preferably below 75.994 kPa, still more preferably below 50.663 kPa, and most preferably under vacuum. The term "vacuum" refers to a pressure below 25 kPa.

The effect is that the final cream comprises less air. The less air there is in the cream, the smoother the cream feels. An additional advance of the low air content in the cream is that in this way, there is less oxygen gas in the cream and less oxidation of the active substance and/or of the adjuvants.

In a preferred embodiment, the mixing of step d) is realized at a lower speed in relation to the mixing speed in step b). The mixing speed in step d) is preferably 10 to 90%, more preferably 20 to 80%, still more preferably 30 to 70%, even more preferably 40 to 60% and most preferably 50% of the mixing speed in step b).

The advantage of a slower mixing speed is that less air is mixed in the cream and that the final cream will comprise less air. The lowering of the mixing speed is only possible because the mixing itself of the suspension and the placebo cream is realized more fluently by increasing the temperature above the melting point of the placebo cream. If this would not be the case, the lowering of the mixing speed would result in a longer mixing time to obtain a cream with the same homogeneity, the longer mixing time introduces more air in the cream. The mixing can be realized by means of a rotor mixer.

In a preferred embodiment, the aqueous phase comprises 70 to 95 percent in weight of glycerol, more preferably 80 to 90 percent in weight of glycerol and most preferably 85 percent in weight of glycerol, expressed in relation to the aqueous phase.

Glycerol fulfils the function of moistening agent in the final cream. It ensures that less water evaporates out of the aqueous phase and that the composition of the cream therefore remains constant for a longer time. This, in turn, maintains the stability of the emulsion and suspension and prevents disintegration when the cream is exposed to the atmosphere for a longer time.

In a preferred embodiment, the aqueous phase comprises polysorbate in an amount of 1 to 15 percent in weight, more preferably 2.0 to 12.0 percent in weight, more preferably 3 to 9 percent in weight, still more preferably 4 to 6 percent in weight and most preferably 5.6 percent in weight in relation to the topical composition. Polysorbate 60 is preferably used, corresponding to 20 groups of polyoxyethylene sorbitan monostearate.

Polysorbate functions as an emulsifier and a surfactant. This ensures the suspension obtained in step a) is homogenous and that it is stabilized against disintegration. The final cream itself will also stabilise by the presence of the polysorbate, preferably polysorbate 60.

The term "white soft paraffin" is a technical term referring to the semi-solid mixture of hydrocarbons. Soft paraffin has its own CAS number, namely 8009-03-8. Petroleum jelly is a synonym and Vaseline® is a trade name under which white soft paraffin is sold. The melting point of white soft paraffin is around the body temperature, preferably between 33° C. and 40° C.

The term "liquid paraffin" is a technical term referring to a refined mineral oil. Liquid paraffin has its own CAS number, namely 8012-95-1. Paraffinum liquidum is a synonym, and paraffinum perliquidum and paraffinum subliquidum are sometimes used to refer to liquid paraffin with a respectively lower or higher viscosity. Liquid paraffin is sometimes referred to by the term paraffin oil. Liquid paraffin is, as the name says, liquid at a room temperature of 21° C.

In a preferred embodiment, the ingredients in step b) comprise one or more ingredients from the list of hexadecanol, paraffin, butylhydroxyanisol, sorbic acid or salt, water, or combinations thereof.

The topical composition preferably comprises 5.0 to 20.0 percent in weight of hexadecanol also known as cetyl alcohol, more preferably 7.5 to 15.0 percent in weight of hexadecanol, more preferably 10.0 to 13.0 percent in weight of hexadecanol and most preferably 11.0 to 12.0 percent in weight of hexadecanol, typically 11.1 percent in weight of hexadecanol, expressed in relation to the total weight of the composition.

The topical composition preferably comprises 1.0 to 15.0 percent in weight of white soft paraffin, more preferably 2.5 to 10.0 percent in weight of white soft paraffin, more preferably 3.5 to 7.5 percent in weight of white soft paraffin and most preferably 5.0 to 6.0 percent in weight of white soft paraffin, typically 5.6 percent in weight of white soft paraffin, expressed in relation to the total weight of the composition.

The topical composition preferably comprises 5.0 to 20.0 percent in weight of liquid paraffin, more preferably 7.5 to 15.0 percent in weight of liquid paraffin, more preferably 10.0 to 13.0 percent in weight of liquid paraffin and most preferably 11.0 to 12.0 percent in weight of liquid paraffin, typically 11.1 percent in weight of liquid paraffin, expressed in relation to the total weight of the composition.

The topical composition preferably comprises 0.001 to 0.010 percent in weight of butyl hydroxyanisol, more preferably 0.002 to 0.008 percent in weight of butyl hydroxyanisol, more preferably 0.003 to 0.006 percent in weight of butyl hydroxyanisol and most preferably 0.004 to 0.005 percent in weight of butyl hydroxyanisol, typically 0.005 percent in weight of hydroxyanisol, expressed in relation to the total weight of the composition.

The topical composition preferably comprises 0.10 to 0.50 percent in weight of sorbic acid or a same equivalent as a salt thereof, more preferably 0.14 to 0.40 percent in weight of sorbic acid, still more preferably 0.17 to 0.30 percent in weight of sorbic acid and most preferably 0.20 to 0.25 percent in weight of sorbic acid or a same equivalent as a salt thereof, the salt of sorbic acid is preferably a salt with an alkali metal cation, more preferably potassium sorbate, expressed in relation to the total weight of the composition.

The topical composition preferably comprises:
5.0 to 20.0 percent by weight of hexadecanol,
1.0 to 15.0 percent by weight of white soft paraffin;
5.0 to 20.0 percent by weight of liquid paraffin;
0.001 to 0.010 percent by weight of butyl hydroxyanisol,
0.10 to 0.50 percent by weight of sorbic acid or an equivalent as salt thereof; and
water.

The topical composition preferably comprises:
7.5 to 15.0 percent by weight of hexadecanol,
2.5 to 10.0 percent by weight of white soft paraffin;
7.5 to 15.0 percent by weight of liquid paraffin;
0.002 to 0.008 percent by weight of butyl hydroxyanisol,
0.14 to 0.40 percent by weight of sorbic acid; and
water.

The topical composition preferably comprises:
11.0 to 12.0 percent by weight of hexadecanol,
5.0 to 6.0 percent by weight of white soft paraffin;
11.0 to 12.0 percent by weight of liquid paraffin;
0.003 to 0.006 percent by weight of butyl hydroxyanisol,
0.17 to 0.30 percent by weight of sorbic acid or an equivalent as salt thereof; and
water.

The topical composition preferably comprises:
5.0 to 20.0 percent in weight of hexadecanol also known as cetyl alcohol, more preferably 7.5 to 15.0 percent in weight of hexadecanol, more preferably 10.0 to 13.0 percent in weight of hexadecanol and most preferably 11.0 to 12.0 percent in weight of hexadecanol, such as 11.1 percent in weight of hexadecanol;
1.0 to 15.0 percent in weight of white soft paraffin, more preferably 2.5 to 10.0 percent in weight of white soft paraffin, more preferably 3.5 to 7.5 percent in weight of white soft paraffin and most preferably 5.0 to 6.0 percent in weight of white soft paraffin, such as 5.6 percent in weight of white soft paraffin;
5.0 to 20.0 percent in weight of liquid paraffin, more preferably 7.5 to 15.0 percent in weight of liquid paraffin, more preferably 10.0 to 13.0 percent in weight of liquid paraffin and most preferably 11.0 to 12.0 percent in weight of liquid paraffin, such as 11.1 percent in weight of liquid paraffin;
0.001 to 0.010 percent in weight of butyl hydroxyanisol, more preferably 0.002 to 0.008 percent in weight of butyl hydroxyanisol, more preferably 0.003 to 0.006 percent in weight of butyl hydroxyanisol and most preferably 0.004 to 0.005 percent in weight of butyl hydroxyanisol;
0.10 to 0.50 percent in weight of sorbic acid or a same equivalent as a salt thereof, more preferably 0.14 to 0.40 percent in weight of sorbic acid, still more preferably 0.17 to 0.30 percent in weight of sorbic acid and most preferably 0.20 to 0.25 percent in weight of sorbic acid or a same equivalent as a salt thereof, the salt of sorbic acid is preferably a salt with an alkali metal cation, more preferably potassium sorbate; and
water.

In a preferred embodiment, sorbic acid is, in step c), in situ formed from a sorbic salt, preferably potassium sorbate, by adding a same equivalent acid, preferably a Brønsted acid, more preferably an inorganic acid, and most preferably hydrochloric acid.

Although the active substance has an antibacterial effect, it does not help with the prevention of the increase of gram negative bacteria, yeasts and fungi. Sorbic acid is however effective in preventing these microbial growth and is therefore preservative. Sorbate salt doesn't have these characteristics and must therefore be transformed into sorbic acid by adding an acid.

In a preferred embodiment, the pH is, after step d), adjusted to a pH value of 4.0 to 5.5, more preferably 4.5 to 5.2 and most preferably 5.0; by adding an acid, preferably a Brønsted acid, more preferably inorganic acid, and most preferably hydrochloric acid.

As a result of the low pH, the preservative works better. At pH values above 5.5, the fungus *Aspergillus niger* can still multiply. However, at pH values under 5.5, the preservative is also effective against *Aspergillus niger*.

In a preferred embodiment, polysorbate is partially added in step a) and partially in step c), preferably 30 to 70% of the amount of polysorbate is added in step a), more preferably 40 to 60% of the amount of polysorbate is added in step a) and most preferably 50% of the amount of polysorbate is added in step a).

As a result, the fusidic acid suspension of step a) as well as the placebo cream of step c) are stabilized and can better be mixed together.

In a preferred embodiment, glycerol is partially added in step a) and partially in step c), preferably 30 to 70% of the amount of glycerol is added in step a), more preferably 40 to 60% of the amount of glycerol is added in step a) and most preferably 50% of the amount of glycerol is added in step a).

The adding of glycerol to the placebo cream ensures that the composition of the placebo cream is closer to the composition of the final cream. The presence of the glycerol also contributes to the stability of the placebo cream.

In a preferred embodiment, the fusidic acid has a particle size with a $D_{90}$ lower than 10 μm. The particle size is measured by means of laser diffraction analysis.

A particle size lower than 10 μm ensures that the active substance has a large surface-to-volume ratio and this has a higher efficiency than an active substance with a low surface-to-volume ratio.

In a second aspect, the invention provides a composition appropriate for topical application, comprising:
  0.5 to 5.0 percent in weight of fusidic acid, more preferably 1.0 to 4.0 percent in weight of fusidic acid, more preferably 1.5 to 3.0 percent in weight of fusidic acid and most preferably 2.0 to 2.5 percent in weight of fusidic acid;
  5.0 to 20.0 percent in weight of hexadecanol also known as cetyl alcohol, more preferably 7.5 to 15.0 percent in weight of hexadecanol, more preferably 10.0 to 13.0 percent in weight of hexadecanol and most preferably 11.0 to 12.0 percent in weight of hexadecanol, such as 11.1 percent in weight of hexadecanol;
  1.0 to 15.0 percent in weight of white soft paraffin, more preferably 2.5 to 10.0 percent in weight of white soft paraffin, more preferably 3.5 to 7.5 percent in weight of white soft paraffin and most preferably 5.0 to 6.0 percent in weight of white soft paraffin, such as 5.6 percent in weight of white soft paraffin;
  5.0 to 20.0 percent in weight of liquid paraffin, more preferably 7.5 to 15.0 percent in weight of liquid paraffin, more preferably 10.0 to 13.0 percent in weight of liquid paraffin and most preferably 11.0 to 12.0 percent in weight of liquid paraffin, such as 11.1 percent in weight of liquid paraffin;
  0.001 to 0.010 percent in weight of butyl hydroxyanisol, more preferably 0.002 to 0.008 percent in weight of butyl hydroxyanisol, more preferably 0.003 to 0.006 percent in weight of butyl hydroxyanisol and most preferably 0.004 to 0.005 percent in weight of butyl hydroxyanisol;
  0.10 to 0.50 percent in weight of sorbic acid or a same equivalent as a salt thereof, more preferably 0.14 to 0.40 percent in weight or sorbic acid, still more preferably 0.17 to 0.30 percent in weight of sorbic acid and most preferably 0.20 to 0.25 percent in weight of sorbic acid or a same equivalent as a salt thereof, the salt of sorbic acid is preferably a salt with an alkali metal cation, more preferably potassium sorbate;
  5.0 to 20.0 percent in weight of glycerol, more preferably 6.5 to 15.0 percent in weight of glycerol, still more preferably 8.0 to 12.0 percent in weight of glycerol and most preferably 9.0 to 10.0 percent in weight of glycerol, such as 9.4 percent in weight of glycerol, glycerol is preferably added to the composition as a 85 percentage in weight solution in water;
  1.0 to 15.0 percent in weight of polysorbate, more preferably 2.5 to 10.0 percent in weight of polysorbate, still more preferably 3.5 to 7.5 percent in weight of polysorbate and most preferably 5.0 to 6.0 percent in weight of polysorbate, such as 5.6 percent in weight of polysorbate, preferably polysorbate 60, also called polyoxyethylene (20) sorbitan monostearate; and
  water;
wherein the homogeneity of the fusidic acid content in the composition is preferably 90% to 110%, more preferably 92% to 108%, still more preferably 94% to 106% and most preferably 96% to 104% of the suggested fusidic acid content; and
the amount of air present in the cream is lower than 5 vol %, preferably lower than 3 vol %, more preferably lower than 2 vol % and most preferably lower than 1 vol %.

The amount of air in the cream is preferably measured as follows:

A volume of cream is placed in a vacuum chamber, the vacuum is generated by a vacuum pump maintaining a maximum pressure of 5 Pa. Between the vacuum pump and the vacuum chamber, a colder finger is provided that is cooled in a bath of 2-propanol, also called isopropanol, with solid carbon dioxide ($CO_2$) ice, also called dry ice. In this way, the cold finger is kept at a constant temperature of −77° C. The cream is placed in the vacuum chamber for 1 hour and mixed at a pace of 2 Hz. After 1 hour in the vacuum chamber, the volume of the remaining cream is determined as well as the volume of the liquid present in the cold finger. The sum of these two volumes is compared to the original volume of cream and the difference in the volume of air that was present in the cream.

The homogeneity of a cream is expressed as an interval, between which the effective concentration of the active substance, here fusidic acid, may vary and to the suggested concentration as a middle point in this interval. The interval is mostly expressed as a percentage in relation to the suggested value. For example, a homogeneity of 90% to 110% refers to a cream wherein an arbitrary chosen sample may have a content of active substances up to 10% under and up to 10% above the suggested content of active substances. In order to determine the homogeneity in a batch of cream, three packings of the final cream are chosen arbitrarily and each time, three samples are taken, one in the bottom of the packing, one in the middle of the packing and one in the upper part of the packing.

These nine samples are analysed to determine the amount of active substance and the extreme value determines the interval defining the homogeneity.

The composition with a high homogeneity and a low amount of air has the advantage that the composition feels smooth and still doesn't lose its homogeneity. A lower homogeneity make a correct treatment more difficult if not impossible because the patient doesn't know how much active substance he/she applies. As a result of a low homogeneity, the effectively applied amount of fusidic acid varies, as a result of which a patient sometimes applies too much and sometimes too little for an effective treatment of his/her complaint. When applying too little fusidic acid, the bacteria do not stop multiplying. Hence, the treatment lasts longer, and the bacteria that are exposed to fusidic acid, can develop resistance. When applying too much fusidic acid, the side effects of fusidic acid such as irritation, itching and redness increase.

In a preferred embodiment, the composition has a pH value of 4.0 to 5.5, more preferably 4.5 to 5.2 and most preferably 5.0.

As a result of the low pH, the preservative, sorbic acid, works better. Only the acid form has the characteristics to serve as a preservative. The non-protonated sorbate form doesn't have preservative characteristics. The $pK_a$ value for sorbic acid is 4.8 as a result of which, almost no acid active form is present at a pH above 5.5, the lower the pH value, the more sorbic acid will effectively be present as the acid active form. At pH values above 5.5, the fungus *Aspergillus niger* can still multiply, however, at pH values under 5.5, the preservative is also effective against *Aspergillus niger*.

In a preferred embodiment, the fusidic acid has a maximum particle size of 10 μm, that is a $D_{90}$ lower than 10 μm. The particle size is measured by means of laser diffraction analysis.

A particle size lower than 10 μm ensures that the active substance has a large surface-to-volume ratio and this has a higher efficiency than an active substance with a low surface-to-volume ratio.

In a preferred embodiment, the composition is produced with a method according to an embodiment of the invention.

This ensures that there is little air in the cream and that still, a high homogeneity is obtained.

In a third aspect, the invention provides a tube made of aluminium comprising a composition according to an embodiment of the invention, wherein the inside of the tube is provided with an epoxy coating.

The use of an epoxy coating ensures that the fusidic acid as well as the adjuvants cannot react with the aluminium of the tube and thus are transformed in impurities that can possibly have a negative side effect on side effects and shelf time.

In a fourth aspect, the invention provides a composition according to an embodiment of the invention for use in the treatment of skin infections caused by bacteria that are sensitive to fusidic acid.

Bacteria that are sensitive to fusidic acid are for example strains from *Neisseria* and gram positive bacteria such as staphylococci, in particular *Staphylococcus aureus, Streptococcus* and *Corynebacterium minutissimum*.

Skin infections caused by bacteria that are sensitive to fusidic acid are for example impetigo, folliculitis, sycosis barbae, paronychia and erythrasma.

In the following, the invention will be described by means of non-limiting examples illustrating the invention, and not meant to be interpreted as limiting the scope of the invention.

Example 1

Table 1 gives a summary of a 2 percent in weight of fusidic acid cream according to an embodiment of the invention.

TABLE 1

Composition fusidic acid cream

| Ingredient | function | mg/g cream |
|---|---|---|
| fusidic acid | active substance | 20.00 |
| hexadecanol | O/W emulsifier | 111.00 |
| white soft paraffin | lipophilic carrier | 56.00 |
| liquid paraffin | lipophilic carrier | 111.00 |
| butyl hydroxyanisol | antioxidant | 0.04 |
| potassium sorbate | preservative | 2.70 |
| glycerol | moistening agent | 94.35 |
| polysorbate 60 | emulsifier, surfactant | 56.00 |
| hydrochloric acid (2M) | pH regulator | to pH 5.0 |
| water | hydrophilic carrier | rest |

Example 2

Table 2 gives a summary of a 1.5 percent in weight of fusidic acid cream according to an embodiment of the invention. This example also shows the benefit of the use of a placebo cream, the latter remains unchanged when the content of fusidic acid is changed.

TABLE 2

Composition fusidic acid cream

| Ingredient | function | mg/g cream |
|---|---|---|
| fusidic acid | active substance | 15.00 |
| hexadecanol | O/W emulsifier | 111.00 |
| white soft paraffin | lipophilic carrier | 56.00 |
| liquid paraffin | lipophilic carrier | 111.00 |
| butyl hydroxyanisol | antioxidant | 0.04 |
| potassium sorbate | preservative | 2.70 |
| glycerol | moistening agent | 94.35 |
| polysorbate 60 | emulsifier, surfactant | 56.00 |
| hydrochloric acid (2M) | pH regulator | to pH 5.0 |
| water | hydrophilic carrier | rest |

Example 3

Table 3 gives a summary of a 3 percent in weight of fusidic acid cream according to an embodiment of the invention.

TABLE 3

Composition fusidic acid cream

| Ingredient | function | mg/g cream |
|---|---|---|
| fusidic acid | active substance | 30.00 |
| hexadecanol | O/W emulsifier | 111.00 |
| white soft paraffin | lipophilic carrier | 56.00 |
| liquid paraffin | lipophilic carrier | 111.00 |
| butyl hydroxyanisol | antioxidant | 0.04 |
| potassium sorbate | preservative | 2.70 |
| glycerol | moistening agent | 94.35 |
| polysorbate 60 | emulsifier, surfactant | 56.00 |
| hydrochloric acid (2M) | pH regulator | to pH 5.0 |
| water | hydrophilic carrier | rest |

Example 4

The creams of example 1, 2 or 3 are produced according to the following method.

A suspension is made of the amount of fusidic acid in the amount of glycerol provided as an 85 percent in weight solution in water. Next, 30% of the amount of polysorbate 60 is added. The latter stabilizes the fusidic acid suspension.

The amounts of hexadecanol, white soft paraffin, butyl hydroxyanisol and the remaining amount of polysorbate 60 are melted and mixed, subsequently, the amount of liquid paraffin is added and a potassium sorbate solution in water is added. All these ingredients are mixed in a rotor mixer and this at a rotor speed of 40 revolutions per minute. Once a white, homogenous mass, the placebo cream, is formed, this mass is heated to 70° C.

At this temperature, the fusidic acid suspension is added to the melted placebo cream and the temperature of the obtained mixture is increased to 72° C. This mixture is subsequently stirred at a rotor speed of 20 revolutions per minute.

The pH value of this mixture is measured and 2 M of hydrochloric acid is added until the pH value is in the interval going from 5.0 up to and including 5.2.

Example 5

A composition according to one of the previous examples is introduced in an aluminium tube, the inside of which is provided with an epoxy coating. The tube itself is closed by a screw cap made of high-density polyethylene (HDPE). These tubes are subsequently packed in a cardboard box together with a leaflet, wherein the cardboard box is made of recycled cardboard.

What is claimed is:

1. Method for the preparation of a topical fusidic acid composition, comprising the steps of:
    a) suspending fusidic acid having a particle size with a $D_{90}$ lower than 10 µm in an aqueous phase to form a suspension;
    b) melting and mixing at least two ingredients to obtain a placebo cream;
    c) heating the placebo cream above its melting point;
    d) mixing the suspension of step a) with the placebo cream of step c) under air at an air pressure of below 25 kPa and at a lower mixing speed than employed in step b);
    wherein the mixing in step d) is realized at a temperature of minimum 5° C. above the melting point of said placebo cream, and is conducted by stirring for a time, stirring speed, and air pressure selected to achieve an amount of air present in the composition of lower than 5 vol %, and wherein polysorbate is partially added in step a) and partially in step c).

2. Method according to claim 1, wherein the aqueous phase comprises 70 to 95 percent in weight of glycerol, expressed in relation to the aqueous phase.

3. Method according to claim 1, wherein the aqueous phase comprises an amount of polysorbate of 1 to 15 percent in weight in relation to the topical composition.

4. Method according to claim 1, wherein the placebo in step b) comprises:
    5.0 to 20.0 percent by weight of hexadecanol,
    1.0 to 15.0 percent by weight of white soft paraffin;
    5.0 to 20.0 percent by weight of liquid paraffin;
    0.001 to 0.010 percent by weight of butyl hydroxyanisol,
    0.1 to 0.5 percent by weight of sorbic acid or an equivalent as salt thereof; and
    water, expressed in relation to the total weight of the topical composition.

5. Method according to claim 1, wherein, in step c), sorbic acid is in situ formed from a sorbate salt by adding a same equivalent of acid.

6. Method according to claim 1, wherein, after step d), the pH is adjusted to a pH value between 4.0 and 5.5 by means of adding an acid.

7. Method according to claim 1, wherein glycerol is partially added in step a) and partially in step c).

* * * * *

UNITED STATES PATENT AND TRADEMARK OFFICE
CERTIFICATE OF CORRECTION

| | | |
|---|---|---|
| PATENT NO. | : 10,420,779 B2 | |
| APPLICATION NO. | : 15/133606 | |
| DATED | : September 24, 2019 | |
| INVENTOR(S) | : Kool | |

It is certified that error appears in the above-identified patent and that said Letters Patent is hereby corrected as shown below:

On the Title Page

Item (12) should read: Kool

Item (72) Please delete: "Thomas Jacobsen, Leuven (BE)", please add: Peter Jan Robert Kool, Melick (NL)

Signed and Sealed this
Fifteenth Day of October, 2024

Katherine Kelly Vidal
*Director of the United States Patent and Trademark Office*